United States Patent [19]

Potucek et al.

[11] Patent Number: 4,732,564

[45] Date of Patent: Mar. 22, 1988

[54] DENTAL IMPLANT ALIGNMENT AND BENDING APPARATUS

[75] Inventors: Frank R. Potucek; Edward J. Smith, both of Clearwater, Fla.

[73] Assignee: Surgical Appliances, Inc., Clearwater, Fla.

[21] Appl. No.: 945,587

[22] Filed: Dec. 23, 1986

[51] Int. Cl.⁴ .............................................. A61C 3/00
[52] U.S. Cl. ..................................... 433/50; 433/176; 433/25; 433/75
[58] Field of Search .................. 433/167, 176, 24, 50, 433/49, 72, 75, 25

[56] References Cited

U.S. PATENT DOCUMENTS 4,109,383 8/1978 Reed et al. ............................ 433/72
4,202,099 5/1980 Roberts ................................ 433/176

Primary Examiner—Gene Mancene
Assistant Examiner—Adriene J. Lepiane
Attorney, Agent, or Firm—Herbert W. Larson; Joseph C. Mason

[57] ABSTRACT

Apparatus includes a mandible alignment device and a jaw pattern jig to prepare a one-piece metal dental implant for insertion into a patient's mouth. The alignment device has a central scissors member with a rear positioned thumb wheel controlling the longitudinal spread of the scissors blades. A front portion of a longitudinal angle adjustment member mounted over the scissors holds an anterior foot portion of a dental implant. A rod integral with the end of each scissors blade supports a housing holding a ramus member portion of a dental implant. After a pattern is determined by the alignment device, it is locked into the jaw pattern jig and the one-piece metal dental implant is bent to shape to substitute for the anterior foot and ramus members removed from the alignment device.

10 Claims, 11 Drawing Figures

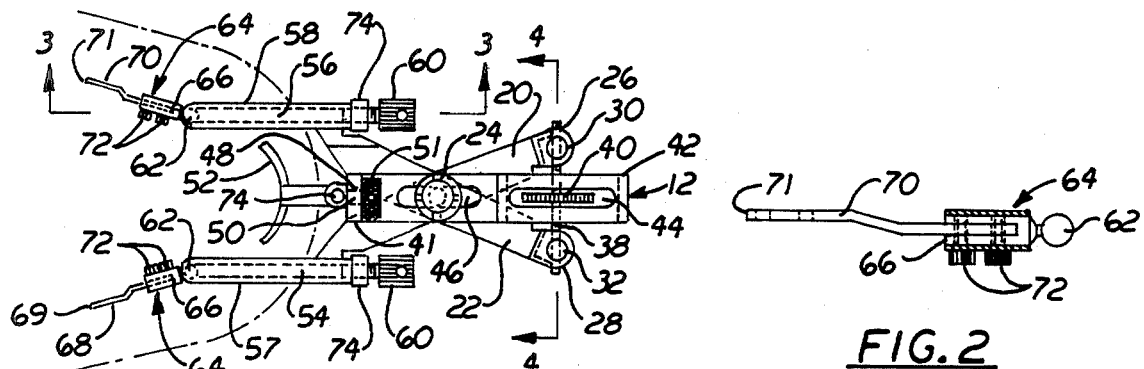
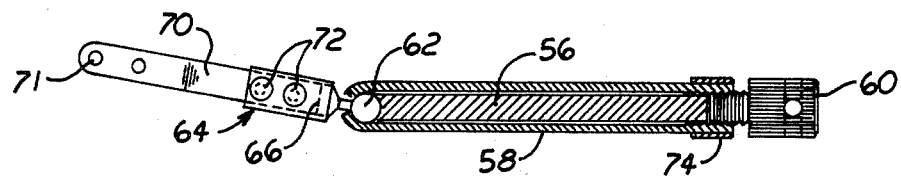
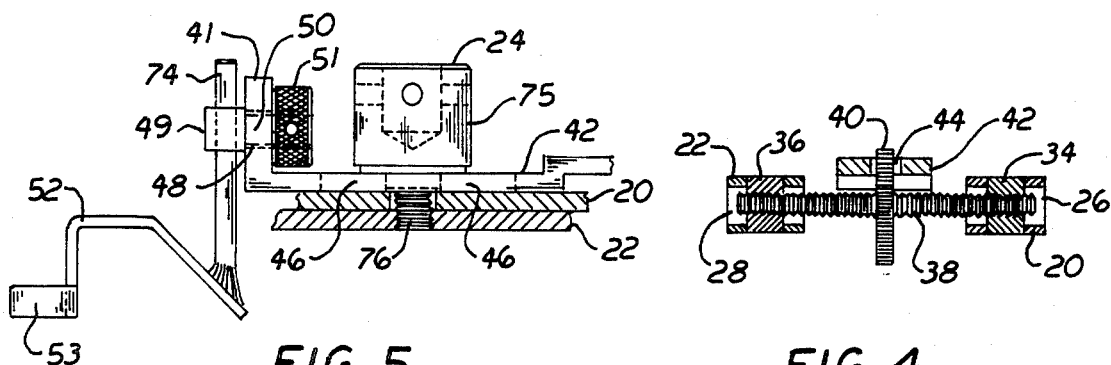

DENTAL IMPLANT ALIGNMENT AND BENDING APPARATUS

BACKGROUND OF THE INVENTION

1. Field of The Invention

This invention relates to devices for bending dental implants. More particularly, it relates to a device and method for precisely aligning and bending a dental implant prior to insertion into the patient's mandible.

2. Description of The Prior Art

Dental support frames or implant devices as described in U.S. Pat. Nos. 3,577,853; 4,202,099 and 4,547,158 are being used with increasing frequency by the dental profession for supporting artificial dentures. These support frames employ a one piece metal bar having substantially the contour of the mandible and having rear extensions implanted into the ascending ramus in the mandible. The implant device must be custom fit to the particular contour of the patient's mandible. This has been done heretofore by starting with a standard implant frame approximating the patient's mandible and bending and adjusting the frame to the exact contour of the patient's mandible. The procedure has been carried out by placing the standard implant into the mouth of the patient and then after estimating the proper alignment bending the frame. The bending and mouth alignment is repeated numerous times until the correct alignment is achieved. This procedure is time consuming and uncomfortable for the patient. A procedure and device is needed to pattern the shape of the patient's mandible in advance and then prepare the precise implant away from the patient.

SUMMARY OF THE INVENTION

We have discovered an apparatus and method for decreasing the time and trauma inflicted on a patient during preparation and sizing of a dental implant.

Our apparatus includes a mandible alignment device having a central scissors member with a rear positioned thumb wheel controlling the longitudinal spread of the scissors blades. A pivot point locking screw locks a longitudinal angle adjustment member into place over the scissor blades. The front of the longitudinal angle adjustment member captures the anterior foot portion of the dental implant. Integral with the end of each scissors blade is a rod. The rod is encased within a housing having a locking screw at a back end and a swivel fitting supporting a pivot element at a front end. The pivot element captures a ramus member portion of the dental implant.

After the pattern of the mandible is determined by our mandible alignment device, it is mounted on a jaw pattern jig and tightened into position. The two dental implant ramus portions and the anterior foot portion are removed and replaced by a one piece metal implant which is bent and trimmed according to the preset pattern on the jig. The formed dental implant is then inserted into the patient's mandible.

DESCRIPTION OF THE DRAWINGS

The present invention may be best understood by those having ordinary skill in the art by reference to the following detailed description when considered in conjunction with the accompanying drawings in which:

FIG. 1 is a plan view of the device of this invention inserted into the mouth of a patient, the mouth outline being shown in phantom lines.

FIG. 2 is a plan view of a pivot element with captured left ramus member.

FIG. 3 is a section view along 3—3 of FIG. 1.

FIG. 4 is a section view along 4—4 of FIG. 1.

FIG. 5 is an elevation view in partial section of a scissors portion of the device of this invention together with the anterior foot portion of the dental implant.

DESCRIPTION OF THE PREFERRED EMBODIMENT

Figure 6:
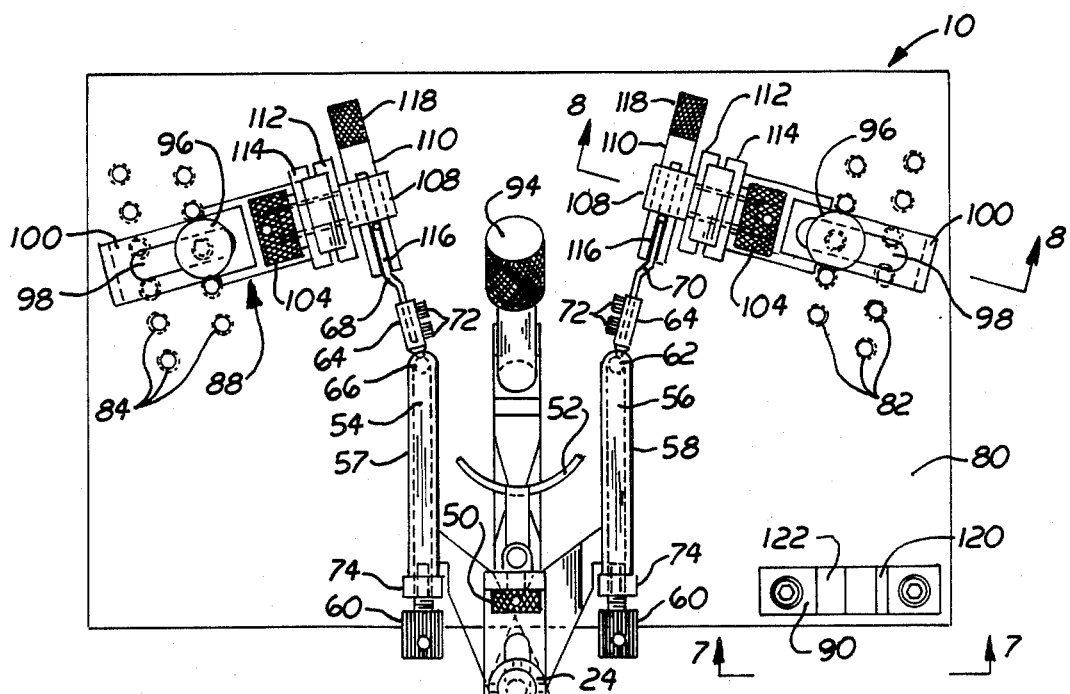
FIG. 6 is a plan view of the device and portions of the implant mounted in a jaw pattern jig.
Figure 7:
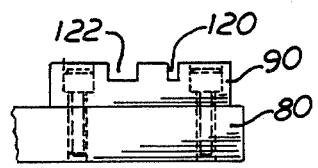
FIG. 7 is a section view in elevation along 7—7 of FIG. 6 showing the bending portion of the jaw pattern jig.

The entire bending apparatus 10 is shown in FIG. 6. The front portion of the measuring device 12 is shown in FIG. 1 placed in the mouth 14 of a patient just above the mandibular bone 16. See also FIG. 11.

The measuring device 12 has a central scissors member 18. This scissors has blades 20 and 22 which move relative to each other below pivot point screw 24. The rear portions 26 and 28 respectively of the scissors 18 have a bore 30 and 32 respectively through which nuts 34 and 36 respectively fit. The nuts engage a right to left screw 38 on which rests and moves a thumb wheel 40.

Above the scissors 18 is a longitudinal angle adjustment plate 42 having a rear slot 44 through which thumb wheel 40 projects and a front slot 46 through which the pivot point screw 24 projects. Movement of thumb wheel 40 in either the right or left direction along screw 38 changes the position of the scissors blades 20 and 22. Release of screw 24 allows the longitudinal plate 42 to move forward and back over the scissors 18. The forward most end of the longitudinal plate 42 contains an upright member 41 with a bore 48 through which a screw 50 passes. The screw is integral with clevis 49 which holds post 74 integral with an anterior foot frame member 52.

Scissors blade 20 is integral with a rod 54 and scissor blade 22 is integral with rod 56. Rod 54 is enclosed by a slotted housing 57 and rod 56 is enclosed by slotted housing 58. Movement of housing 57 or 58 is controlled by a locking screw 60 engaging threads at a first end. At a second end of the housing 57 or 58 is a swivel fitting 62 which is locked in place by rod 54 or 56. The swivel fitting 62 is integral with a pivoting locking element 64. Each locking element 64 contains a slot 66 through which a ramus member portion of a dental insert is inserted. A right ramus member 68 is controlled by the swivel arrangement in housing 57 and the left ramus member 70 is controlled by the swivel mechanism in housing 58. Each of the locking elements 64 have a pair of screws 72 which tighten and hold down the respective right and left ramus members 68 and 70. Housing 57 or 58 is tightened down over rods 54 and 56 respectively as a result of turning locking screw 60. Bushing 74 keeps the slotted housing 57 or 58 from spreading. By release of locking screw 60 either on the housing 57 or 58 the respective ramus members are adjusted into the ascending ramus of the patient's mouth. Tightening locking screw 60 locks right or left ramus member 68 or 70 into a fixed position.

Member pieces 52, 68 and 70 are used as a guide to duplicate the exact positioning and pattern of the incision in the mandible in the patient's mouth. By firmly setting each of members 52, 68 and 70 within mandible alignment device 12, these positions can be precisely duplicated.

The exact position of the anterior foot 52 can be determined by an up and down movement along post 74. Once the correct height of anterior foot 52 is achieved, nut 51 is tightened down. The tightening of nut 51 pulls post 74 in next to the face of upright member 41. Locking screw 24 is tightened down when the exact relationship of anterior foot 52 has been achieved with respect to the two ramus members 70 and 68. The alignment of the two ramus members can be achieved in part by movement of thumb wheel 40 which controls the spread of scissors 18. Tightening down on nut 51 and screw 24 sets the exact position. Screw head 75 on screw 24 has an integral thread 76 which follows a bore hole in scissor blades 20 and 22 respectively. The bottom of screw head 75 rests on the surface of plate 42 with slot 46 on each side.

The distal ends 69 and 71 of ramus member 68 and 70 respectively are inserted into a bony incision made in each ascending ramus. The distal end 69 or 71 is inserted about 12 mm into this incision taking due care to avoid hitting the inferior alveolar nerve and artery. The bottom 53 of anterior foot 52 is inserted into a bony incision made in the mandible symphysis.

Figure 9:
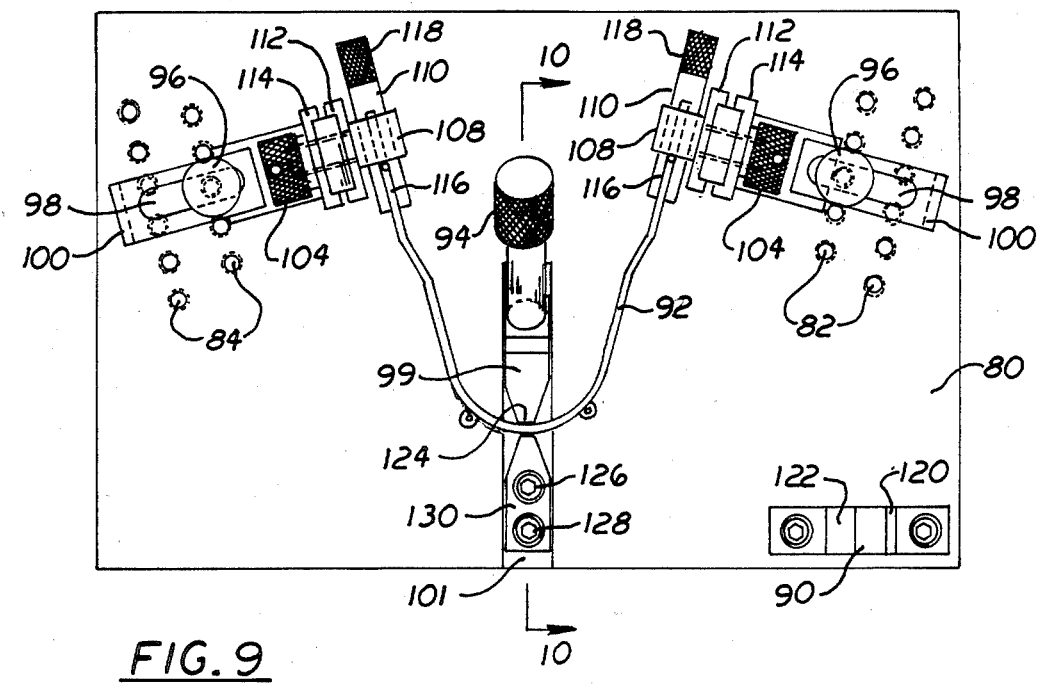
FIG. 9 is a plan view of a one piece metal implant bent according to the jaw pattern jig.

After the alignments are made over the mandible, the alignment device 12 is locked in place over jaw pattern jig plate 80 as shown in FIG. 6. The jig plate 80 has a built-in set of holes 82 corresponding to the left side of the mandible and adjusting holes 84 corresponding to the right side of the mandible. A positioning device 86 on the right side of jig plate 80 locks the left side ramus member 70 into place and the locking device 88 on the left side of the jig plate 80 locks the right side ramus member 68 into place. A bending device 90 is located on the plate 80 for convenience to bend the one piece metal implant 92 as seen in FIG. 9.

The alignment device 12 is tightened onto jig plate 80 in the first instance by vice tightening screw 94 having a nut 95 located in a hole 97 in the bottom of jig 80. Block 99 resting in slot 101 moves toward slot 124 upon tightening screw 94.

Figure 8:
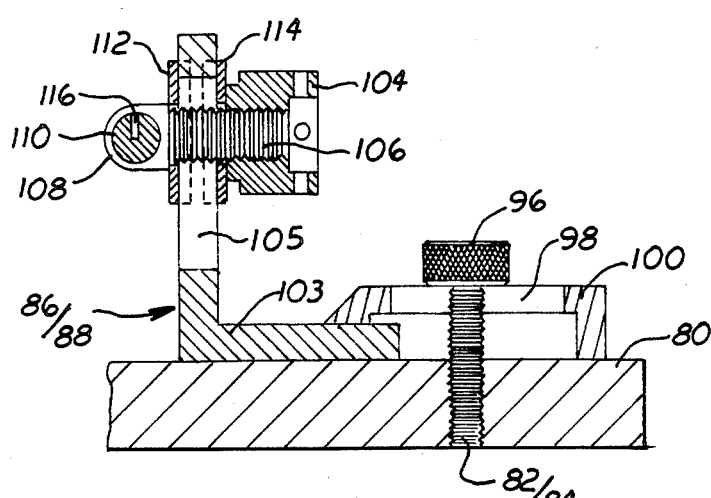
FIG. 8 is a section view in elevation along 8—8 of FIG. 6 showing a locking clamp on the jaw pattern jig.

The right 68 and left 70 ramus member positions are determined by the positioning devices 88 and 86 respectively. Both positioning devices 88 and 86 are the same and will be described as such. The positioning device is set in a hole 84 or 82 in the jig plate 80 by positioning screw 96 which slides in slot 98 in clamp 100. As seen in FIG. 8 screw 96 holds down clamp 100 over L-shaped member 103. L-shaped member 103 has a slot 105. Nut 104 engages threads 106 integral with a locking clevice 108 which captures positioner shaft 110 to position the ramus member 68 or 70 in slot 116. Shaft 110 is rotatable 360° and is further movable to align pitch angle. The screw threads 106 of locking clevis 108 pass through plates 112 and 114. Positioner shaft 110 is pressed by clevis 108 into plate 112 by turning nut 104. A finger hold 118 integral with shaft 110 allows it to be turned in a clockwise or counterclockwise direction. Tightening down on nut 104 sets the device in a fixed position.

Figure 10:
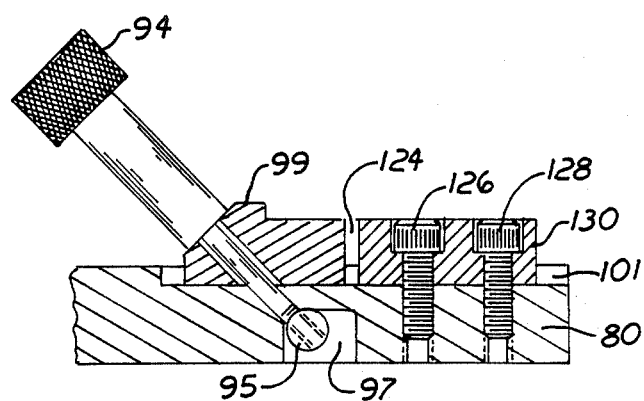
FIG. 10 is a section view in elevation along 10—10 of FIG. 9.
Figure 11:
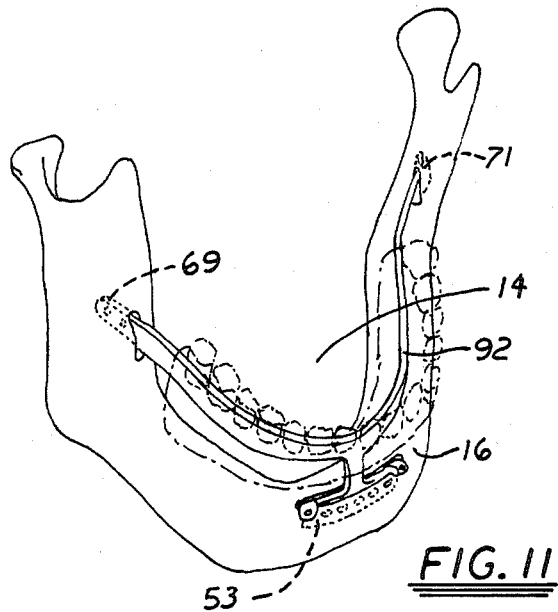
FIG. 11 is a perspective view of the implant inserted into a mandible.

After the alignment device 12 is fixed in place over jig 80 the ramus members 68 and 70 and the anterior front foot 52 are removed. At this point a one piece metal implant 92 of choice is fitted to the pattern set on jig plate 80 as seen in FIG. 9. Dental implant device 92 is bent to the correct alignment using bending device 90 which has slots 120 and 122 to assist in the bending operation. As shown in FIG. 10 vice tightening screw 94 can be tightened down to close down slot 124 to hold the anterior front portion of the dental implant 92 in place. Screws 126 and 128 hold block 130 in place in slot 101 over jig plate 80. Although the bending of the dental implant 92 must be done in a trial and error fashion until it completely conforms to the pattern set in jig plate 80, such maneuver is much shorter than carrying it out in the mouth of the patient. It also avoids an extremely uncomfortable and traumatic procedure for the patient. After removing the dental implant 92 from the clamping members on jig plate 80 it is ready for inserting into the mandible as shown in FIG. 11.

If the ends of the standard dental implant are too long, they can be cut off in a die and the ends smoothed prior to use. The die used to cut the ends of the dental implant has a stop corresponding to the relative position of anterior foot 52 mounted on alignment device 12. This determines the exact measurement for cutting the ramus ends of the implant. Holes are punched in the ends of the implant to allow for growth of bone through the holes and insure better anchoring of the implant.

The method of this invention duplicates outside the mouth in the dental implant device the exact depth of the bony incision in the right and left ramus and symphysis. In addition, the placement of the incisions and angulation with respect to the respective incisions and the structure of the mandible is exactly replicated outside the mouth of the patient.

Substitution of equivalent devices and methods may be carried out without departing from the scope of this invention.

Having thus described the invention, what is claimed and desired to be secured by Letters Patent is:

1. Dental implant aligning device for duplicating the alignment of the component parts of a patient's mandible comprising:
    (a) a scissors member having two crossing blades with front and rear ends, the front end of each blade integral with a rod enclosed within a movable housing and the rear end of the blades bridged by a screw member having a centering thumb wheel mounted on the screw,
    (b) a front and back movable longitudinal adjustment plate mounted over the scissors, the plate having a rearwardly directed slot enclosing the thumb wheel and a front member adjacent an anterior foot portion of the aligning device; and
    (c) the movable rod housing having a means at a rear end for advancing or retracting the housing in relation to the rod, the movable housing having a swivel fitting mounted in a front end, the swivel fitting integral with a locking element capable of capturing a ramus member portion of the aligning device.

2. A dental implant aligning device according to claim 1 wherein the front member of the longitudinal adjustment plate is L-shaped with a bore through an upright arm, a threaded screw integral with a clevis mounted in the bore, a ring portion of the clevis outboard of the upright arm and a nut inboard of the upright arm mounted on the screw so that turning of the nut causes a post captured by the clevis and integral with the anterior foot to be pulled in against the upright arm.

3. A dental implant aligning device according to claim 2 wherein the swivel fitting in the movable housing is ball shaped and the locking element contains a slot for capturing an anterior end of a ramus member.

4. A dental implant aligning device according to claim 3 wherein the means for advancing or retracting the movable housing is a screw threaded to an interior portion of the housing at the rear end so that tightening of the screw presses the swivel fitting against a front end of the rod and prevents movement of the swivel fitting.

5. A dental implant aligning device in combination with a jaw pattern jig to establish the alignment of a one piece metal mandible implant comprising:
   (a) as part of the jaw pattern jig a base plate having multiple left and right spaced apart bores,
   (b) a left and right positioning device, each positioning device having a means, affixed to the base plate by a screw engaged to one of the bores, for supporting a position shaft having a slot for capturing a distal end of a ramus member,
   (c) an anterior end of each ramus member being captured by a locking element of the implant aligning device,
   (d) the implant aligning device having a scissors member with two crossing blades, a front end of each blade integral with a rod enclosed within a movable housing, the movable housing having a front mounted swivel fitting integral with the locking element,
   (e) a longitudinally movable adjustment plate mounted over the scissors and supporting a rod integral with an anterior foot member of the dental implant at a front end,
   (f) a vice tightening screw mounted on the jaw pattern jig between the scissors blades of the implant aligning device, the vice tightening screw moving a first block in a slot of the jig to capture the anterior foot between the first block and a second block permanently affixed to the slot in the jig, the position of the implant aligning device together with the ramus members and anterior foot member being thereby precisely aligned.

6. A dental implant aligning device in combination with a jaw pattern jig according to claim 5 wherein the means for supporting the position shaft is a clamp affixed to the base plate by a first screw engaged to one of the bores, the clamp holding down an L-shaped element of the positioning device containing a slot in an upright member to allow a second screw integral with a clevis capturing the position shaft to be engaged to a nut for tightening the position shaft against the upright member.

7. A dental implant aligning device in combination with a jaw pattern jig according to claim 5 wherein a rear end of the longitudinal movable adjustment plate contains a slot through which a thumb wheel riding on a third screw projects the turning of the screw controlling the distance between the rods on each end of the scissors blades.

8. A dental implant aligning device in combination with a jaw pattern jig according to claim 5 wherein the front end of the movable adjustment plate is L-shaped with a bore through an upright member, a clevis integral with a screw passing through the bore and engaging a nut on an inboard side of the upright member, the clevis capturing an upright post on an outboard side of the upright member, the post being integral with the anterior foot member.

9. A method of conforming and placing a one piece metal dental implant into a patient's mandible comprising:
   (a) capturing separated right and left ramus members and an anterior foot portion of a dental implant in a mandible aligning device;
   (b) matching the right and left ramus members and anterior foot portion of a dental implant to the patient's mandible using aligning adjustments on the aligning device;
   (c) further adjusting the alignment of the right and left ramus members and anterior foot portion of the dental implant into a precise pattern by three dimensional adjustments of the aligning device;
   (d) anchoring the mandible aligning device on a jaw pattern jig having a pair of positioning devices mounted in bores in the jig to hold right and left distal ends of each ramus member, the jig having a vice tightening screw moving a first block to captive a lower end of the anterior foot member between the first block and a second block, substituting for the right and left ramus and anterior foot members a one piece metal implant that is bent and shaped to conform with the pattern set in the jig by the right and left ramus members and anterior foot member;
   (e) removing the one piece metal implant and inserting it into precut incisions in the mandible.

10. A method according to claim 9 wherein the right and left ramus members are captured by separate locking elements of the aligning device and the anterior foot portion is captured by a front portion of a longitudinal angle adjust plate of the aligning device.

* * * * *